United States Patent [19]
Cuschieri et al.

[11] Patent Number: 6,077,286
[45] Date of Patent: Jun. 20, 2000

[54] INSTRUMENT WITH A BENDABLE HANDLE

[75] Inventors: Alfred Cuschieri, St Andrews; Tim Frank, Wormit, both of United Kingdom

[73] Assignee: Karl Storz GmbH & Co. KG, Germany

[21] Appl. No.: 09/180,389

[22] PCT Filed: May 7, 1997

[86] PCT No.: PCT/DE97/00910

§ 371 Date: May 13, 1999

§ 102(e) Date: May 13, 1999

[87] PCT Pub. No.: WO97/41783

PCT Pub. Date: Nov. 13, 1997

[30] Foreign Application Priority Data

May 7, 1996 [DE] Germany .......................... 196 18 291

[51] Int. Cl.[7] .............................. A61B 17/32; A61B 1/00; A61B 1/267
[52] U.S. Cl. .................. 606/170; 606/174; 600/104; 600/197
[58] Field of Search ...................................... 606/170, 174; 600/104, 197

[56] References Cited

U.S. PATENT DOCUMENTS

| 4,950,273 | 8/1990 | Briggs ........................ 606/113 |
| 5,752,973 | 5/1998 | Kieturakis ........................ 606/207 |
| 5,836,960 | 11/1998 | Kolesa et al. ........................ 606/170 |

*Primary Examiner*—Linda C. M. Dvorak
*Assistant Examiner*—Jocelyn Debra Ram
*Attorney, Agent, or Firm*—St.Onge Steward Johnston & Reens LLC

[57] ABSTRACT

What is described here is an instrument having a shaft element carrying an engaging element disposed on the distal end thereof, which is operated via a proximally disposed actuator element which is integrated into a handle for being mobile in such a way that the angle enclosed by the axis of said handle and by the axis of said shaft element may be varied. The invention is characterized by the provision that the handle is connected to the shaft element via a universal joint.

15 Claims, 1 Drawing Sheet

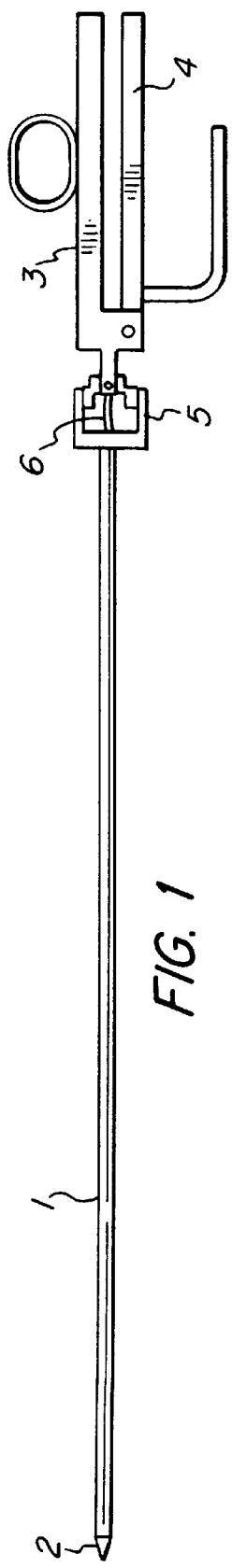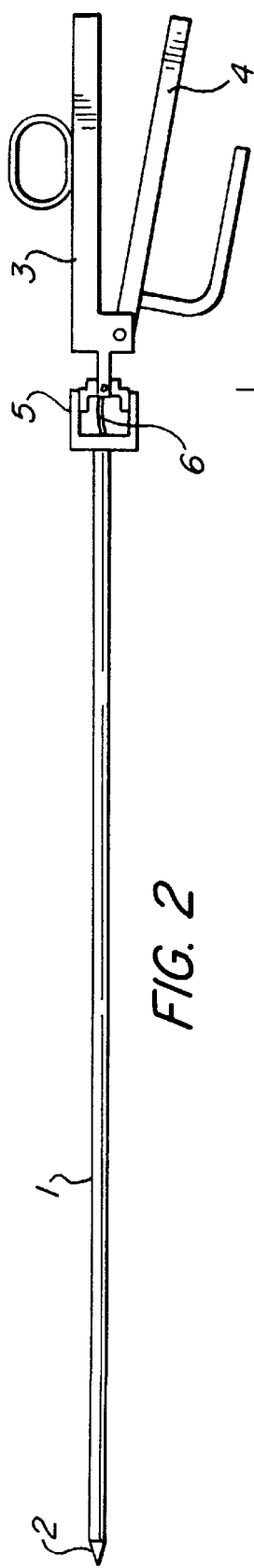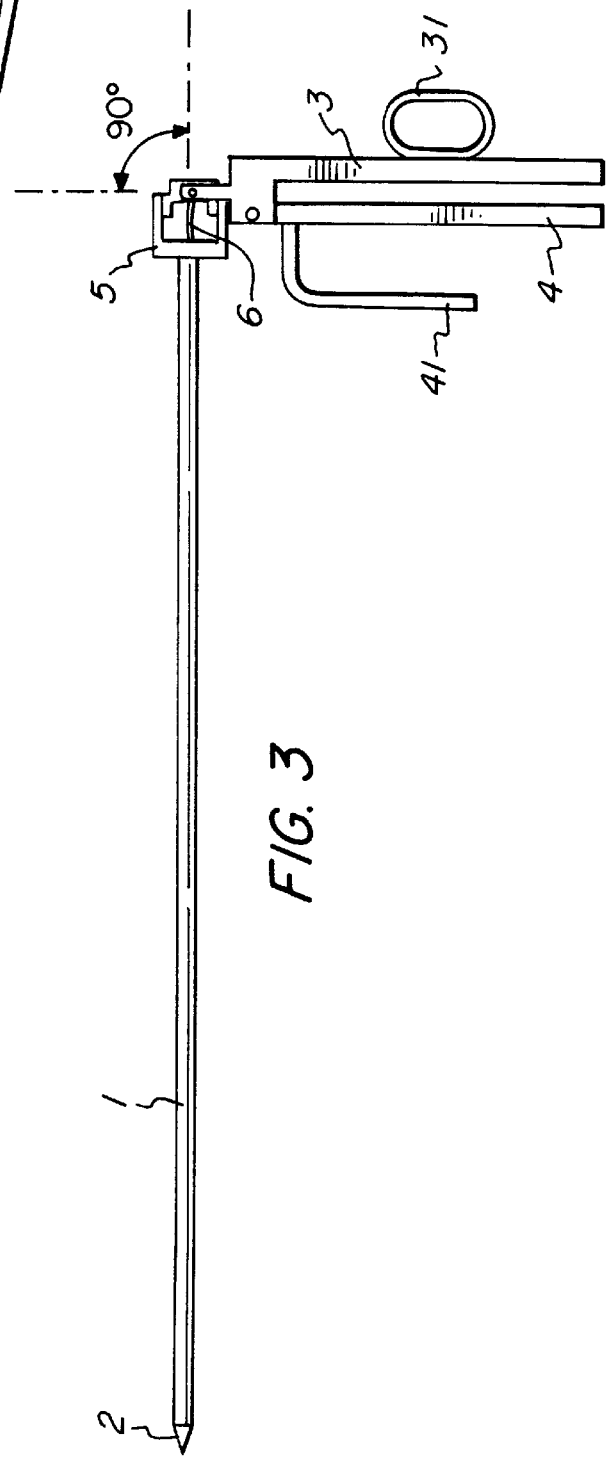

INSTRUMENT WITH A BENDABLE HANDLE

DESCRIPTION

1. Field of the Invention

The present invention relates to an instrument for engaging an object upon actuating a remote activating element which is integrated into a displaceable handle of the instrument.

2. Prior Art

Instruments having a shaft element carrying an engaging element on its distal end, which is operated by a proximally disposed actuator element integrated into a handle are generally common in the field of bioengineering and particularly in endoscopy. Reference just by way of an example is made to tubular shaft instruments produced by Karl Storz GmbH & Co., Tuttlingen, Germany. Explicit reference is made to these instruments also as far as all other details are concerned which are not described here in all their details.

In the majority of the known instruments the handle is fixedly mounted on the instrument so that the axis of the handle and the longitudinal axis of the instrument shaft enclose a predetermined invariable angle. This angle is selected for a particular handling of the instrument in consideration of ergonomic aspects.

In the course of a surgical operation, however, working situations may occur in which the predetermined angle between the handle and the shaft renders handling more complicated.

The U.S. Pat. No. 5,395,367 proposes an instrument in which the angular position of the handle may be adjusted relative to the shaft before a surgical operation is performed. Even though the operator can hence match the angular position with the individual requirements unforeseen operating conditions may yet result in the fact that the adjusted angular position, which can practically not be changed during the operation, is inexpedient from an ergonomic point of view.

BRIEF DESCRIPTION OF THE INVENTION

The present invention starts out from the finding that it may actually be necessary in theatre practice to operate an instrument, which is inserted, for instance, into a trocar sleeve or an instrument shaft, with a position of the hand other than that which the designer had assumed in the design of the instrument or which was expected before the operation when the angular position was determined.

The invention is therefore based on the problem of improving an instrument of the type described hereinabove in such a way that the handle position relative to the instrument shaft can be easily adjusted even in the course of an operation so as to permit an ergonomically expedient operation of the instrument independently of the respective surgical or application requirements.

For a solution to the inventive problem the invention starts out from an instrument in which the handle is mounted on the shaft element for movement in such a way that the angle enclosed between the handle axis and the axis of the shaft element may be varied.

In accordance with the present invention the handle is connected to the shaft element via a universal joint. The use of a universal joint presents the advantage that the universal joint can be easily adjusted even under the conditions of a surgical operation and in the associated stress situation so that an optimum adjustability of the handle position relative to the shaft is ensured. Moreover, a universal joint permits the adjustment of the position of the handle in "all directions", relative to the shaft of the instrument, so that not only the angular position may be changed.

It is an aim to achieve a suitable adjustment of the handle position relative to the longitudinal axis of the shaft element as a function of the operating conditions occurring as a result of the respective handling required for the surgical operation, such that the operator can, from an ergonomic point of view, expediently operate the instrument independently of the respective application.

With these provisions in particular it is hence possible to arrange the handle in such a way that its axis encloses an angle between 0° and 90° relative to the longitudinal axis of the shaft element.

In an improvement the handle may be rotated about the longitudinal axis of the shaft element due to the configuration of the universal joint. Even though the relative rotation between the handle and the shaft has been implemented already in certain instruments it entails particular ergonomic advantages, however, in combination with the inventive setting of the angle between the handle and the shaft.

The inventive angular adjustment allows for ergonomic operation in any situation in the course of a surgical operation. Under certain situations, however, it may be inexpedient that the position of the handle relative to the shaft of the instrument can be changed "too easily", which is the result of a universal joint which can be easily adjusted on principle.

In another embodiment therefore provisions are made for locking the handle in a certain angular position or at a defined angle of rotation about the longitudinal axis when the handle can be turned.

The provision of a flexible power transmitting element for transmission of the operating force from the actuator element to the shaft element also contributes to the ergonomic operability of the invention. The power transmitting element may be a Bowden control cable in particular.

The basic inventive idea to be able to vary the angle, which is enclosed by the axis of the shaft, i.e. the longitudinal axis of the instrument and the axis of the handle, freely even during a surgical operation can be fundamentally applied also on the most different instruments. The application of this basic idea is particularly expedient in tubular shaft instruments such as those employed in endoscopy, i.e. on instruments adapted for insertion into the passage of an endoscopic insert instrument such as a trocar sleeve.

BRIEF DESCRIPTION OF THE DRAWING

In the following, the invention will be described in more details by an exemplary embodiment, without restriction of the general inventive idea, with reference to the drawing which is explicitly referenced in all other respects as far as the disclosure of all inventive details is concerned which are not explained thoroughly in the text. In the drawing:

FIG. 1 shows an embodiment of an inventive instrument in the non-operated condition, FIGS. 2 represents the embodiment illustrated in FIG. 1, however in the operated condition, and FIG. 3 shows the embodiment illustrated in FIG. 1 in a condition in which the handle is bent through 90°.

DESCRIPTION OF AN EMBODIMENT

The Figures illustrate an embodiment of an inventive instrument. The instrument includes a shaft element 1 having an engaging element 2 disposed on its distal end. In the illustrated embodiment the engaging element 2 is a provided in the forms of tongs jaws, without any restriction of the general inventive idea. The engaging element 2, i.e. the tongs jaws, is operated by a proximally disposed actuator element.

FIG. 1 shows the tongs jaws in the closed condition whereas FIG. 2 illustrates the tongs jaws in the opened condition.

In the illustrated embodiment the actuator element is a handle consisting of two handpieces 3 and 4. The handpiece 3 is stationary—relative to the handle as a unit—and comprises a "finger ring" 31 through which the thumb of the operator's hand is typically passed. In the illustrated embodiment the mobile handpiece 4 includes a finger shackle 41 which permits an opening of the tongs jaws and which when closed prevents the finger bearing against it, i.e. typically the index finger or the middle finger, from sliding off.

In the illustrated embodiment the handle consisting of the handpieces 3 and 4 is connected to the shaft element via a universal joint 5 which may be moved in all directions.

On account of this universal joint 5 the handle 3, 4 is disposed on the shaft element 1 for movement in such a way that the angle enclosed by the axis of the handle 3, 4 and the axis of the shaft element 1 may be varied. In FIGS. 1 and 2 the angle is 0° and in FIG. 3 the angle is 90°.

With the joint 5 being a universal joint for movement in all directions the handle 3, 4 may be additionally rotated about the longitudinal axis of the shaft element 1 so that the handle may be placed in any optional angular position, without the necessity to rotate the shaft.

It is hence possible to set the shaft of the instrument and particularly to rotate it such that the tongs jaws are placed in the desired position relative to the tissue whilst at the same time the handle is carried in an ergonomically expedient position in which, for instance, the operator can easily apply the required force for an incision.

A flexible power transmitting element 6 is provided in the joint 5, which transmits the operating force exerted by the handpieces 3 and 4, to the shaft element 1. This flexible power transmitting element is a Bowden control cable which, in co-operation with the universally adjustable universal joint, provides the operator with any freedom whatsoever in the adjustment of the orientation of the handle relative endoscopic instrument illustrated in the Figures has a distal end 1 which is with respect to its angular position relative to the longitudinal axis and its rotational position about the longitudinal axis.

The invention has been described in the forgoing with reference to a particular embodiment, without any restriction of the general inventive idea. The most different variations may, however, be made, of course:

Preferably the handle may be adapted to be locked in a certain angular or rotational position, respectively. This may be implemented, for instance, by means of a locking screw which locks the joint 5. The screw is preferably so configured that it may be opened and tightened again in the course of a surgical operation, even without tools.

Other instruments, too, such as HF struments, may be equally instead of the tubular shaft instrument. It is most preferable, however, to configure the respective instrument in a way that it may be inserted into the passage of an endoscopic insert instrument such as a trocar sleeve.

We claim:

1. Instrument including a shaft element having an engaging element disposed on its distal end, which is operated via an actuator element integrated into a handle which is so connected, via a universal joint, to the shaft element that the handle is adapted for movement in a way that an angle enclosed by an axis of the handle and an axis of the shaft element is variable, comprising a flexible power transmitting element extending through said universal joint and said shaft element and transmitting force from said actuator element to said engaging element, said handle being adapted for being locked in a defined position.

2. Instrument according to claim 1, characterized in that a flexible power transmitting element is provided which transmits force from said actuator element to said shaft element.

3. Instrument according to claim 1, characterized in that said handle is designed for rotation about the axis of said shaft element.

4. Instrument according to claim 1, characterized in that a locking screw is provided for locking said universal joint.

5. Instrument according to claim 1, characterized in that the instrument is a tubular shaft instrument.

6. Instrument according to claim 1, characterized in that the instrument is so configured that it can be inserted into an endoscopic insert instrument.

7. Instrument including a shaft element having an engaging element disposed on its distal end, which is operated via an actuator element integrated into a handle which is so connected, via a universal joint, to the shaft element, which is aligned with the universal joint, that the handle is adapted for movement in a way that an angle enclosed by an axis of the handle and an axis of the shaft element is variable, comprising a flexible power transmitting element extending through said universal joint and transmitting force from said actuator element to said engaging element, said handle being adapted for being locked in a defined position.

8. Instrument according to claim 7, characterized in that said handle is designed for rotation about the axis of said shaft element.

9. Instrument according to claim 7 characterized in that a locking screw is provided for locking said universal joint.

10. Instrument according to claim 7, characterized in that the instrument is a tubular shaft instrument.

11. Instrument according to claim 7, characterized in that the instrument is so configured that it can be inserted into an endoscopic insert instrument.

12. Instrument including a shaft element having an engaging element disposed on its distal end, which is operated via an actuator element integrated into a handle which is so connected, via a universal joint, to the shaft element that the handle is adapted for movement in a way that an angle enclosed by an axis of the handle and an axis of the shaft element is variable, comprising a flexible power transmitting element which extends through said universal joint and through said shaft aligned with the universal joint and transmits force from said actuator element to said engaging element, said handle being adapted to be locked in a defined position and being designed for rotation about the axis of said shaft element.

13. Instrument according to claim 12, characterized in that a locking screw is provided for locking said universal joint.

14. Instrument according to claim 12, characterized in that the instrument is a tubular shaft instrument.

15. Instrument according to claim 12, characterized in that the instrument is so configured that it can be inserted into an endoscopic insert instrument.

* * * * *